United States Patent [19]

Comparetto

[11] Patent Number: 4,501,268
[45] Date of Patent: Feb. 26, 1985

[54] BONE WEDGE GUIDANCE SYSTEM

[76] Inventor: John E. Comparetto, P.O. Box 433, Nassawadox, Va. 23413

[21] Appl. No.: 294,653

[22] Filed: Aug. 20, 1981

[51] Int. Cl.³ .............................................. A61F 5/04
[52] U.S. Cl. ................................ 128/92 E; 128/92 H
[58] Field of Search ............. 128/92 EB, 92 E, 92 R, 128/317, 305, 92 H

[56] References Cited

U.S. PATENT DOCUMENTS

| D. 245,918 | 9/1977 | Shen | 128/92 EB |
| 4,069,824 | 1/1978 | Weinstock | 128/317 |
| 4,150,675 | 4/1979 | Comparetto | 128/305 |
| 4,312,079 | 1/1982 | Dörre et al. | 128/92 E |
| 4,349,058 | 9/1982 | Comparetto | 128/305 |

OTHER PUBLICATIONS

Comparetto, John E. "The Osteoguide System", Comparetto Ideas, Inc., Box 433, Nassawadox, VA 23413.

Primary Examiner—John D. Yasko
Assistant Examiner—C. W. Shedd
Attorney, Agent, or Firm—Shoemaker and Mattare, Ltd.

[57] ABSTRACT

A wedge guide of specific angular dimensions allows the excision of a precise bone wedge by the alternate use of a crescentic and planar saw in a stable and accurate manner.

20 Claims, 18 Drawing Figures

BONE WEDGE GUIDANCE SYSTEM

THE BACKGROUND OF THE INVENTION

This patent application is being filed as a continuation in part of Ser. No. 127,010 Matrix Guide For A Precise Crescentric Wedge Ledge Osteotomy.

The wedge guide of this application allows the surgeon to make the surgical osteotomy invented by Comparetto and previously made with the cutting blade of U.S. Pat. No. 4,150,675, by more commonly used means i.e. crescentic and planar saws. This present guide described herein is a preferred embodiment since it presents a more stable means for making the osteotomy. A still greater advantage is the less than 90° curved osteotomy with a slanted to the vertical planar section to thwart upward dorsal grade displacement of the healingly positioned bony parts of the osteotomy.

OBJECT OF THE INVENTION

An object of the invention is to provide a scalar means on the sides of the guide cylinder.

Another object of the invention is to provide a thicker more sturdy single tab means.

Another object of the invention is to provide individual degree guides. A still further object of the invention is to provide a stable wedge guide that has cylindrical and planar tab means that resist unwanted movement when making the planar cuts.

Another object of the invention is to provide a planar cutting guide that forms an acute angle with the curved cut.

A still further object of the invention is to provide a slanted from vertical planar cut that increases resistance to dislodgement of the healingly positioned bone parts. A still further object of the invention is to provide an adjustable planar tab means to yield varying wedge sizes for different degrees of correction.

A still further object of the invention is to provide multiple slot means for the placement of stabilizing tab means as well as cutting blades.

BRIEF DESCRIPTION OF THE DRAWINGS

FIG. 9 shows in schematic form how the wedge is obtained by the first and second planar cuts.

DETAILED DESCRIPTION OF THE INVENTION

Figure 1:
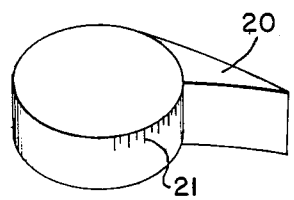
FIG. 1 is a perspective view of an embodiment of a guide that fits within or over a crescentic blade.

The original patent application showed a scale on the upper surface of the cylinder. Closely relating to this a scalar means can be placed on the wall of the cylinder. FIG. 1 shows a single tab means 20 to guide a planar cutting blade having a scalar means 21 on the cylinder wall. For purposes of tab means strength FIG. 1 also shows a thicker tab configuration than in the previous application.

Figure 1A:
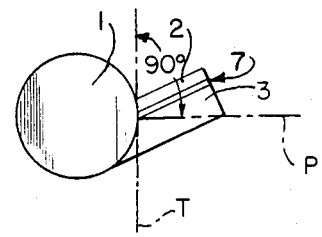
FIG. 1A is a view from above of an osteoguide.

The following descriptions relate to an improved embodiment of the first wedge guide. FIG. 1A is a view from above of the guide cylinder 1 which is of the same circumference as that of a matching crescentic blade. For example, an 18 mm crescentic blade forms a cut that would be an arc of an 18 mm guide cylinder. Off the cylinder's circumference is a degree block comprised of sections 2 and 3. Slot 7, FIG. 1A, can be at any angle to a tangent of the cylinder surface. In FIG. 1A it is depicted as less than 90°. Although the slot could be equal to, less than or greater than 90° the advantage of using an angulation of less than 90° important because this will form a novel semi-curved Vee osteotomy that has greater stability.

Figure 2:
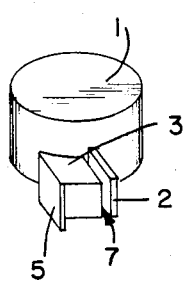
FIG. 2 is a perspective view of an osteoguide showing the guide slot and planar tab means.

FIG. 2 shows a perspective view of the degree block showing the short straight tab 5 that extends below the level of both the degree block and the bottom of the cylinder for several millimeters.

Figure 3:
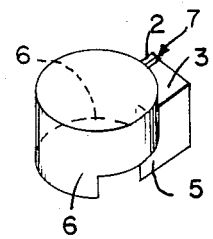
FIG. 3 is a perspective view of an osteoguide showing the curved tab means.

FIG. 3 is an additional perspective view that shows a long curved tab 6 that extends along an arc of the cylinder below the bottom of the cylinder. The long curved tab 6 is longer in longitudinal dimension than the short straight tab 5 coming off the degree block as can be seen in FIG. 4.

Figure 4:
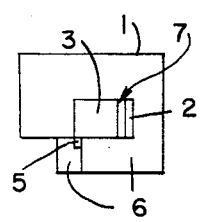
FIG. 4 is a side elevational view showing the relative positions of the tab means.

FIG. 4 is a planar cross sectional view of the wedge guide showing the long curved tab 6, short straight tab 5, degree block portions 2 and 3, slot 7 and cylinder 1 in their relative positions. The long curved tab 6 has an arc less than the width of the crescentic blade to which it's cylinder is matched in circumference; thus it will be readily apparent that the long curved tab can therefore fit into the osteotomy cut of the crescentic blade it corresponds to. The crescentic blades now available to the practitioner are approximately 18 mm, 15 mm, 10 mm, 9 mm, and 8 mm in width from one end of the arc to the opposite end of the arc. The osteotomy cut is made by the oscillation of this blade against the bone, there is therefore a certain amount of travel so that the cut itself is several millimeters larger longer than the respective blade.

Figure 5:
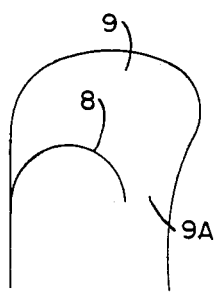
FIG. 5 shows a dorsal view of a crescentic cut in bone.

The bone 9 is cut from one side into and usually beyond the central axis of the bone as depicted in FIG. 5.

Figure 6:
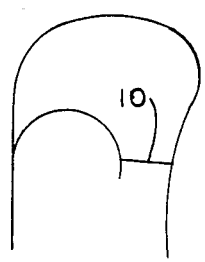
FIG. 6 shows a planar cut in relation to the curved cut of FIG. 5 from a dorsal view.
Figure 7:
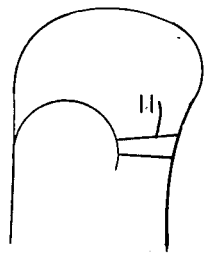
FIG. 7 shows a second planar cut in relation to the first planar cut of FIG. 6 from a dorsal view.
Figure 8:
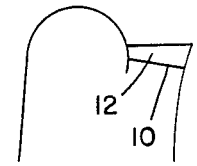
FIG. 8 shows the wedge of bone obtained from the cuts of FIGS. 5-7 from a dorsal view.

The crescentic cut 8 goes all the way through the bone. The bone remains in one piece due to the lack of severence of the opposite side 9A of bone from where the crescentic cut was made. The wedge guide of specific degrees, that corresponds to the crescentic blade used for the osteotomy cut is selected and the long curved tab 6 thereof is placed within the curved slot in the bone as made by the crescentic blade. Then the wedge guide is rotated toward the internal end of the crescentic cut until it can be turned no further; in this illustration clockwise. At this point slot 7 is near the internal end of the crescentic cut. Utilizing an oscillating or sagittal planar saw, the first planar cut in the bone is made by placing the blade within slot 7 of the guide. This cut 10, shown in FIG. 6, is made half way through the bone. The guide cylinder 1 with its long curved tab 6 within the crescentic cut is now turned in the opposite direction from the internal end of the crescentic cut until the short straight tab 5 fits over the partial first straight cut 10 made by the planar blade. The short straight tab 5 is now pressed down into this first straight partial cut. The short straight tab 5 is a precise number of degrees away from the slot 7. A third cut 11, FIG. 7, which is the second straight cut will be made this number of degrees away from the first planar cut. This third cut 11 which is the second straight cut is made all the way through the bone. The wedge guide can now be removed from the osteotomy site and the first straight cut 10 can be completed through the bone, (FIG. 8), thus yielding the precise wedge 12. The bony parts can now be rotated until the ledges formed by the planar cuts are opposed in the corrected position.

Figure 9:
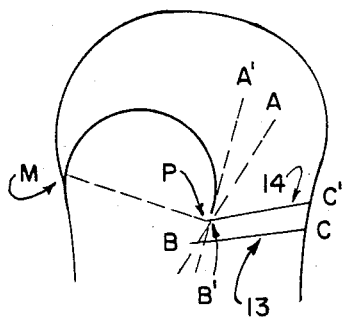
FIG. 9 shows a planar cut that is less than 90° of the crescentic tangent.

FIG. 1A depicts a wedge guide with a slot means 7 at less than 90° to a tangent of the cylinder at its intersection with the cylinder. An example of the osteotomy with this slot means can be seen in FIG. 9. FIG. 9 shows the first planar cut 13 with angle ABC less than 90°. It further shows a precise wedge made from the second planar cut formed by acute and equal angle A'B'C'.

A line MP, FIG. 9, drawn through the ends of the crescentic cut is not perpendicular to the long axis of the bone and therefore allows the planar cuts 13 and 14 to be within a more advantageous position. If points M and P were at a perpendicular to the long axis of bone the acute planar cuts would travel up through the articular surfaces which would be undesirable.

The acute planar cut in combination with the crescentic cut forms not only the precise wedge but a novel "curved-vee" osteotomy that establishes a moment of force around the curvature into the apex of the Vee, which gives great stability and some natural fixation.

Figure 4A:
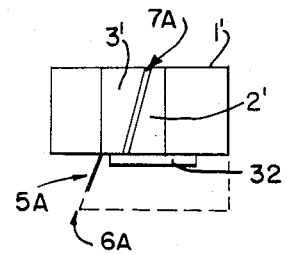
FIG. 4A depicts an embodiment having a slanted slot and planar tab means.
Figure 4B:
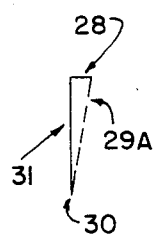
FIG. 4B shows the slanted cut respective to the internal end of the curved cut.
Figure 4C:
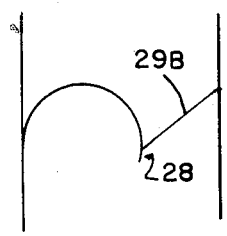
FIG. 4C shows the end of the planar cut internal to the end of the curved cut from a dorsal view.

In FIG. 4A a less than vertical slot means 7A is a precise number of degrees away from an identically slanted straight tab means 5A. To allow for the straight planar cut to meet the crescentic cut along a slanted course the curved tab means must have a slant or an elongation 6A at its periphery that will accomodate the deepest portion of the straight cut. In FIG. 4C, section 28, of the crescentic cut shows the dorsal junction of the planar cut leaving section 28 as a lead for the slanted cut 29A shown in FIG. 4B. Slanted cut 29A reaches the bottom end of crescentic cut 31 at point 30, (FIG. 4B).

Figure 10:
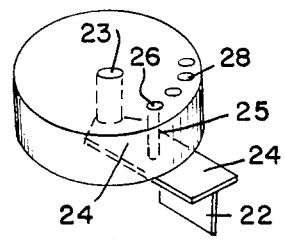
FIG. 10 shows a perspective view of an adjustable planar tab osteoguide.

FIG. 10 shows a perspective view of an adjustable osteoguide that is capable of moving tab element 22 a multiple number of degrees relative to the slot means. Section 23 shows a central axis on which tab platform 24 can be rotated and affixed by rod 25 and screw 26 through a multitude of holes 28 in the cylinder surface.

Figure 11:
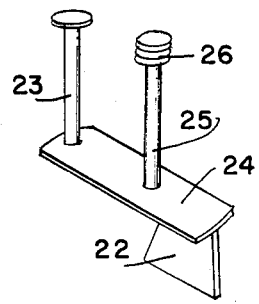
FIG. 11 shows the pin screw mechanism for the moveable tab.

FIG. 11 shows the screw and rod mechanism inserted into platform 24.

Figure 12:
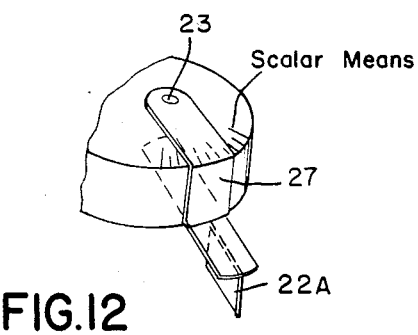
FIG. 12 shows an additional embodiment of adjustment means for a moveable tab.
Figure 13:
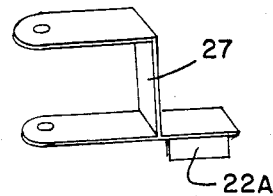
FIG. 13 shows the clip mechanism that holds the planar tab of the FIG. 12 embodiment.

FIG. 12 is another additional embodiment of an adjustable osteoguide having a clear plastic guide clip 27 that can be adjustably rotated a precise numbers of degrees around the cylinder. FIG. 13 is an isolated view of clip 27 per se.

Figure 14:
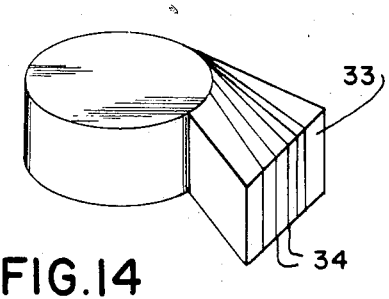
FIG. 14 is a perspective view of another additional embodiment of an adjustable osteoguide that has multiple slot means.

FIG. 14 shows a degree block 33 with multiple slots 34 that are used in the one instance by a removable straight tab means for locking the first planar cut prior to making the second cut through any of the other slots 34 which are precise numbers of degrees from each other.

From the foregoing description, one skilled in the art can easily ascertain the essential characteristics of this invention and without departing from the spirit and scope thereof can make various changes and modifications of the invention to adopt to its various surgical uses.

I claim:

1. An osteotomy guide apparatus for use in a surgical method for changing the axial alignment of a bone having a longitudinal axis by severing said bone and healingly repositioning the resulting segments thereof with respect to each other, which method includes cutting across a portion of said bone in an arcuate cut extending from and through one side of said bone and terminating between said side and the opposed side of said bone, the arc of said arcuate cut being a portion of a circle which has its center offset from said longitudinal axis; and cutting two non-radially extending, circumferentially spaced cuts from said arcuate cut to and through the opposed side of said bone to form a removable wedge so that the severed bone segments can be rotated about said arcuate cut to effect said repositioning when said wedge is removed; said osteotomy guide apparatus comprising: a crecentric curvilinear body having a curvilinear edge extending therefrom for inserting in a crecentric osteotomy cut in a bone, and having a tab planar cut guide means extending outward from the curvilinear body at an angle to the curvilinear body other than normal to a tangent to the body at the intersection of the tab planar cut guide means and the body.

2. The apparatus of claim 1 wherein the tab planar cut guide means has a thickness to accommodate multiple slots, and a plurality of slots being provided.

3. The apparatus of claim 1 wherein said angle is less than 90°.

4. The apparatus of claim 3 wherein the tab planar cut guide means includes a slot for guiding a planar saw.

5. The apparatus of claim 3 wherein the tab planar cut guide means comprises a block having first and second sides and respectively contiguous thereto first and second sections spaced by a slot in said block.

6. The apparatus of claim 5 wherein said slot is located closer to said second side such that the second section is relatively thin compared with the first section.

7. The apparatus of claim 6 wherein the first section has a tab portion extending therefrom which is contiguous said first side; said curvilinear edge and said tab portion being simultaneously insertable respectively in said arcuate cut and a first cut of said two non-radially extending cuts so that said slot is properly located with respect to said first cut so that a cutting instrument may be guided by said slot to make the second of said two non-radially extending cuts in said bone.

8. The apparatus of claim 7 wherein said curvilinear edge extends into the bone further than said tab portion.

9. The apparatus of claim 5 wherein the extended tab portion is angularly oriented with respect to the sides of the block and wherein the guide slot in the block is oriented at a similar angle.

10. The apparatus of claim 5 wherein the tab planar cut guide means includes plural slits spaced from the slot for selectively receiving an extended tab portion for fitting into one of the slits and fitting into a planar cut in the bone concurrently.

11. The apparatus of claim 1 wherein the curved extended edge portion and an extended tab portion are adjustable relative to each other so that a thickness of wedge removed from a bone may be precisely controlled.

12. The apparatus of claim 11 wherein the extended tab portion is angularly adjustable with respect to the body.

13. The apparatus of claim 12 wherein the extended tab portion comprises means for pivoting an inner portion of the tab portion with respect to the body and means for locating an intermediate portion thereof with respect to the body.

14. The apparatus of claim 13 wherein the means for locating an intermediate portion comprises a pin extending substantially parallel to a pivot for said pivot means at the inner portion of the tab portion, and means to secure the pin to an outer portion of the body and intermediate portion of the tab.

15. The apparatus of claim 13 wherein a scale is provided adjacent an outer curvilinear edge of the body and an indicator is connected to the tab portion adjacent the scale.

16. Osteotomy guide apparatus comprising a cap-like body having a cylindrical top, an outer wall circumferentially around said top, a curvilinear extension from a substantial circumference of the outer wall which terminates opposite said outer wall top in a curvilinear edge, tab block means connected to the body and extending outward from the outer wall, the tab block means having a planar cutting guide slot therein for guiding a planar cutting saw, the tab block means further having a locating blade means projecting therefrom for entry into a first planar cut when the curvilinear edge is inserted in a crecentric cut whereby the slot in the tab block means may be precisely aligned for a desired second planar cut.

17. The apparatus of claim 16 wherein the locating blade means is adjustable with respect to the body and the slot.

18. The apparatus of claim 17 wherein the locating blade means is pivotally connected to the body and is fixable in different positions with respect to the body.

19. The apparatus of claim 16 wherein the tab block means includes plural slits spaced from the slot whereby the tab blade is insertable in and extends from a selected slit.

20. The apparatus of claim 16 wherein a portion of the curvilinear edge extends from the body for a first distance and wherein the locating blade means extends from the tab block means for a distance less than the first distance.

* * * * *